(12) United States Patent
Hori et al.

(10) Patent No.: US 7,782,463 B2
(45) Date of Patent: Aug. 24, 2010

(54) PARTICLE DENSITY MEASURING PROBE AND PARTICLE DENSITY MEASURING EQUIPMENT

(75) Inventors: Masanu Hori, Nagoya (JP); Seigo Takashima, Nagoya (JP); Hiroyuki Kano, Aichi (JP); Shoji Den, Yokohama (JP)

(73) Assignees: Nu ECO Engineering Co., Ltd., Nishikamo-gun, Aichi (JP); KATAGIRI Engineering Co., Ltd., Yokohama-shi, Kanagawa (JP)

(*) Notice: Subject to any disclaimer, the term of this patent is extended or adjusted under 35 U.S.C. 154(b) by 415 days.

(21) Appl. No.: 11/987,264

(22) Filed: Nov. 28, 2007

(65) Prior Publication Data

US 2009/0237667 A1    Sep. 24, 2009

(30) Foreign Application Priority Data

Mar. 26, 2007 (JP) .............................. 2007-078267

(51) Int. Cl.
*G01N 21/00* (2006.01)
*G01B 9/02* (2006.01)
*G01J 3/45* (2006.01)
*H05B 31/26* (2006.01)
*H01J 7/24* (2006.01)

(52) U.S. Cl. .................. 356/440; 356/451; 315/111.21

(58) Field of Classification Search .................. 356/128, 356/326, 337, 437, 440; 315/111.21
See application file for complete search history.

(56) References Cited

U.S. PATENT DOCUMENTS

| | | | | |
|---|---|---|---|---|
| 4,576,692 A | * | 3/1986 | Fukuta et al. ................ 204/165 |
| 4,986,658 A | * | 1/1991 | Kim ............................ 356/318 |
| 6,339,297 B1 | * | 1/2002 | Sugai et al. ............. 315/111.21 |
| 6,744,211 B2 | * | 6/2004 | Sugai et al. ............. 315/111.21 |
| 2002/0047543 A1 | * | 4/2002 | Sugai et al. ............. 315/111.21 |
| 2008/0000585 A1 | * | 1/2008 | Kim et al. ............... 156/345.48 |
| 2009/0133471 A1 | * | 5/2009 | Brinkmann ................ 73/30.04 |
| 2009/0237667 A1 | * | 9/2009 | Hori et al. ................... 356/437 |

FOREIGN PATENT DOCUMENTS

JP          2004-354055          12/2004

* cited by examiner

*Primary Examiner*—Patrick J Connolly
(74) *Attorney, Agent, or Firm*—McGinn IP Law Group, PLLC

(57) ABSTRACT

Disclosed is a particle density measuring probe for measuring the density of atoms or molecules in a plasma atmosphere by absorption spectroscopy. The probe has a cylindrical light guiding member provided in the plasma atmosphere. At the front end of the light guiding member, there is provided a reflection plate for reflecting light that has propagated through the cylindrical light guiding member. Behind the reflection plate, in a cross section perpendicular to the longitudinal direction of the light guiding member, a part devoid of a portion of wall surface is provided by a predetermined length in the longitudinal direction. A plasma introducing portion allows mutual contact between light passing through this part devoid of a portion of wall surface and atoms or molecules in the plasma atmosphere. The probe has a main body that guides light in an axial direction by total reflection by a side wall, and that is located behind the plasma introducing portion.

9 Claims, 9 Drawing Sheets

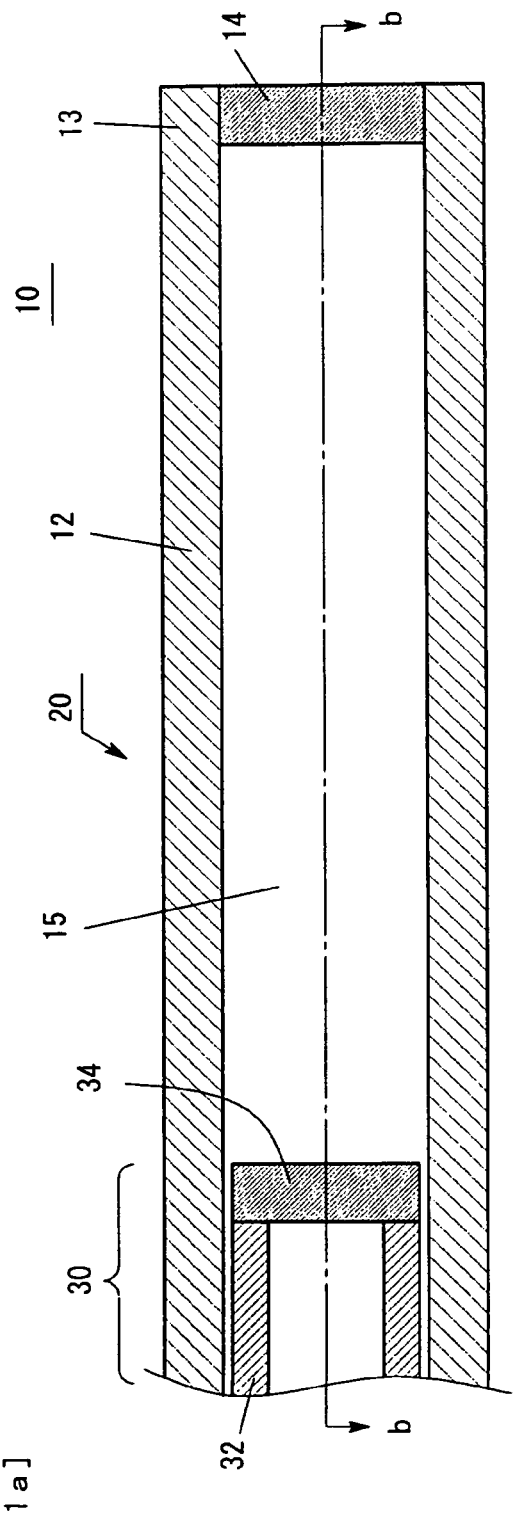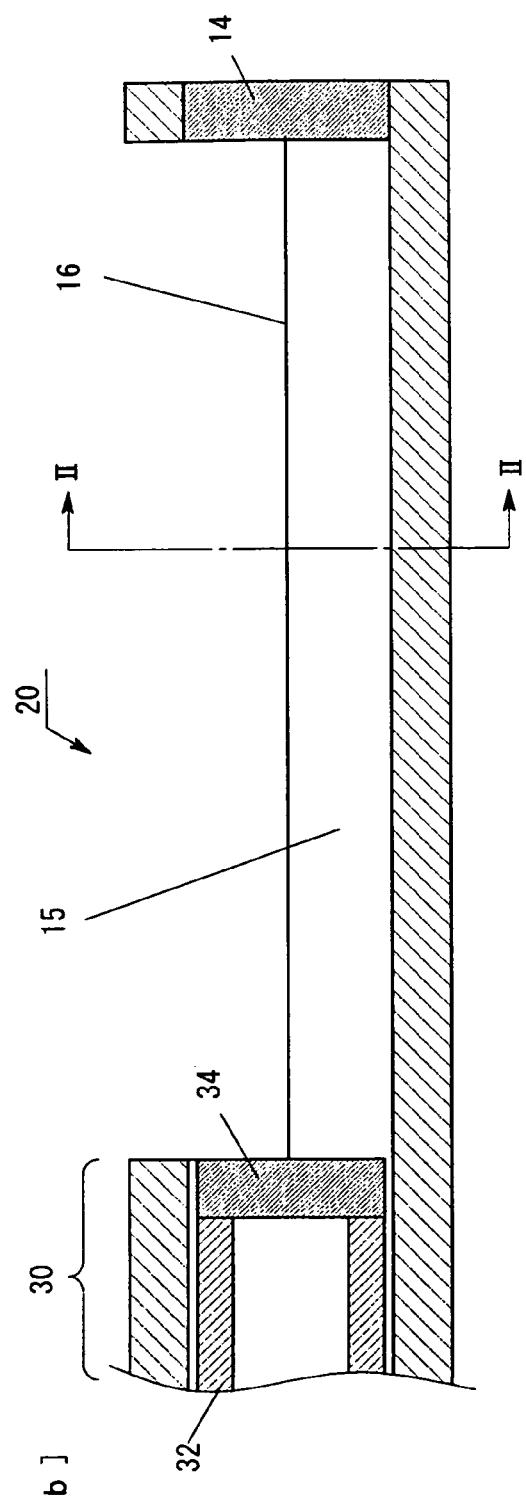

[Fig. 2]
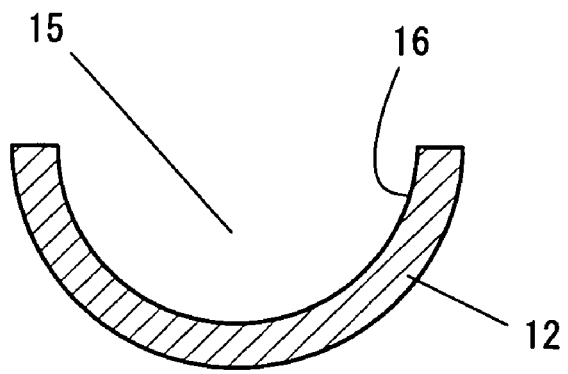
[Fig. 3]
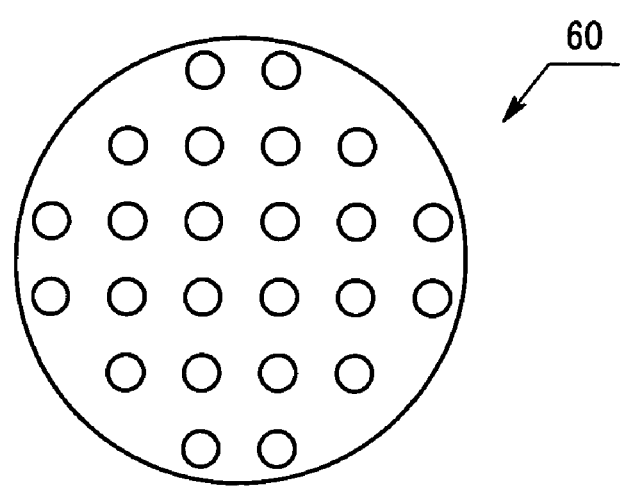

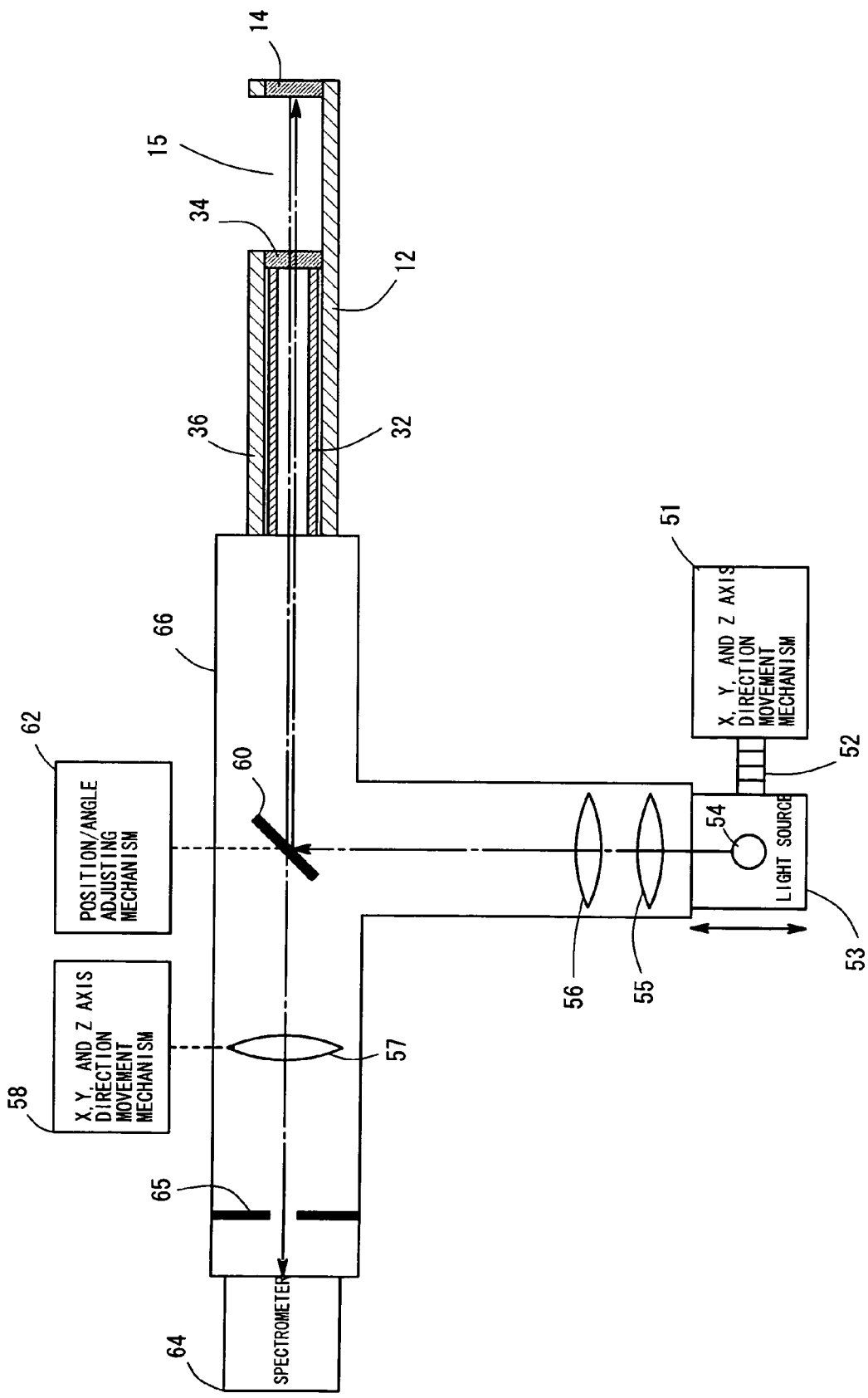
[Fig. 4]

[Fig. 5]
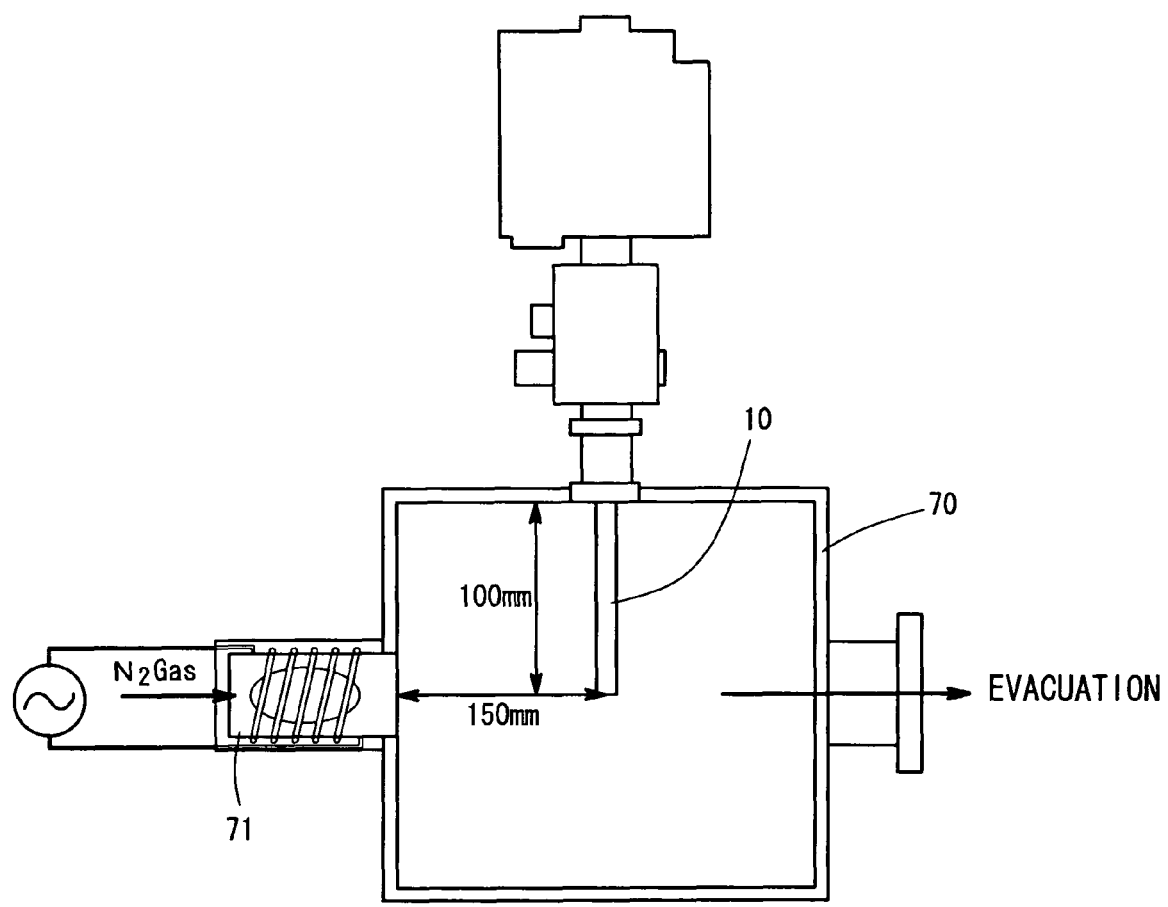

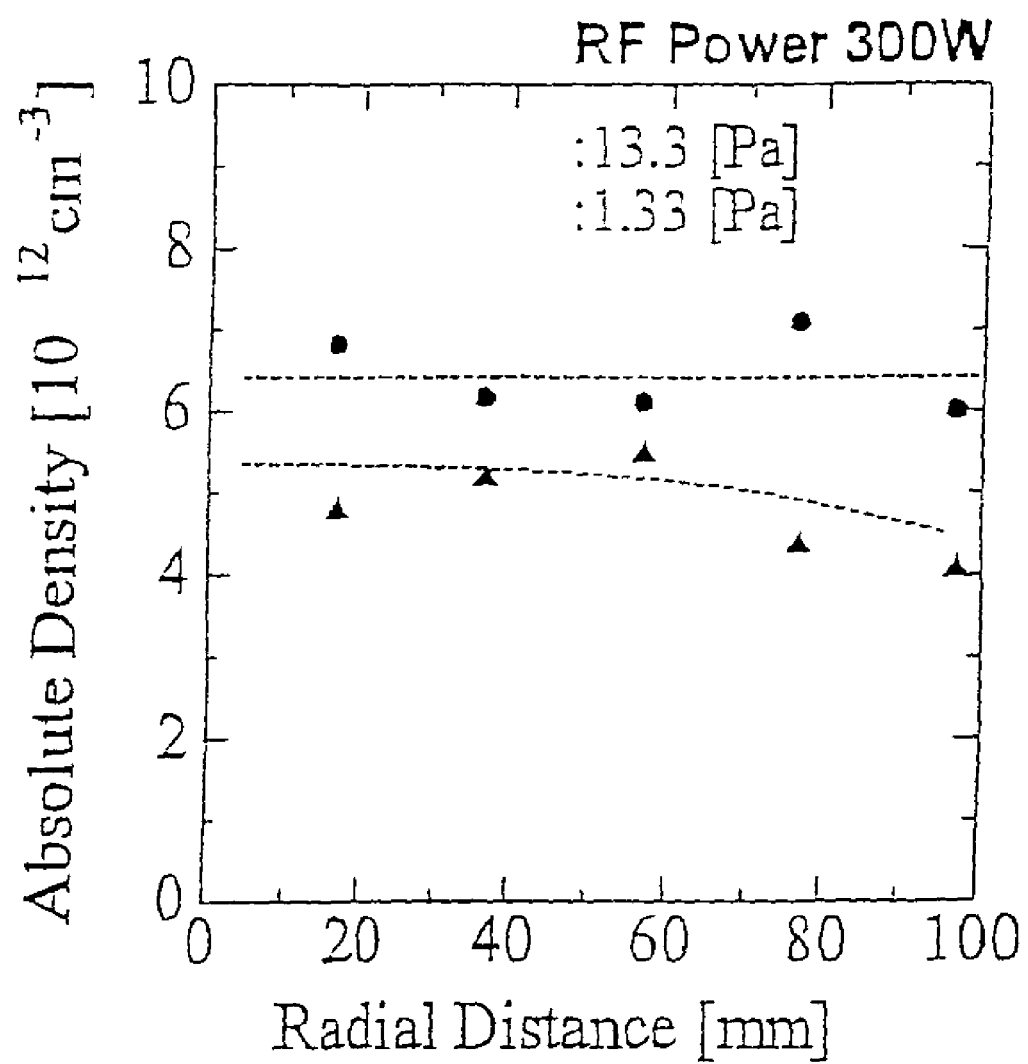
[Fig. 6]

[Fig. 7]
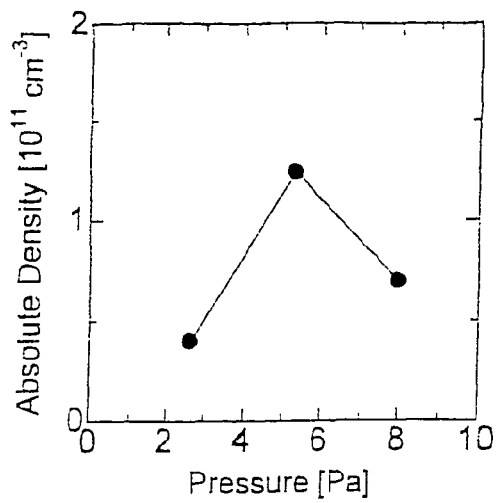
[Fig. 8]
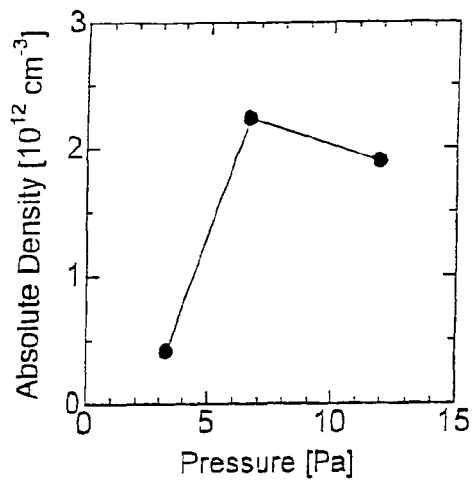
[Fig. 9]
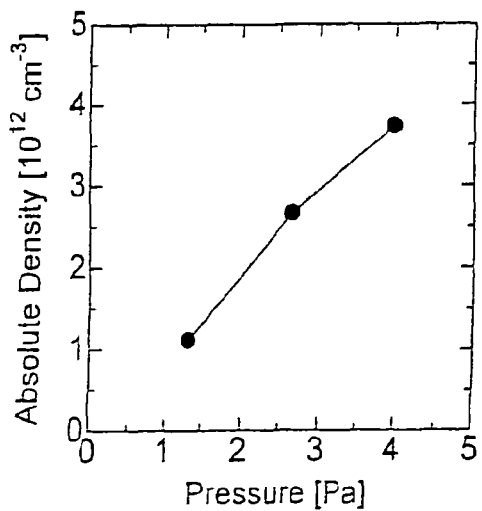

[Fig. 10]
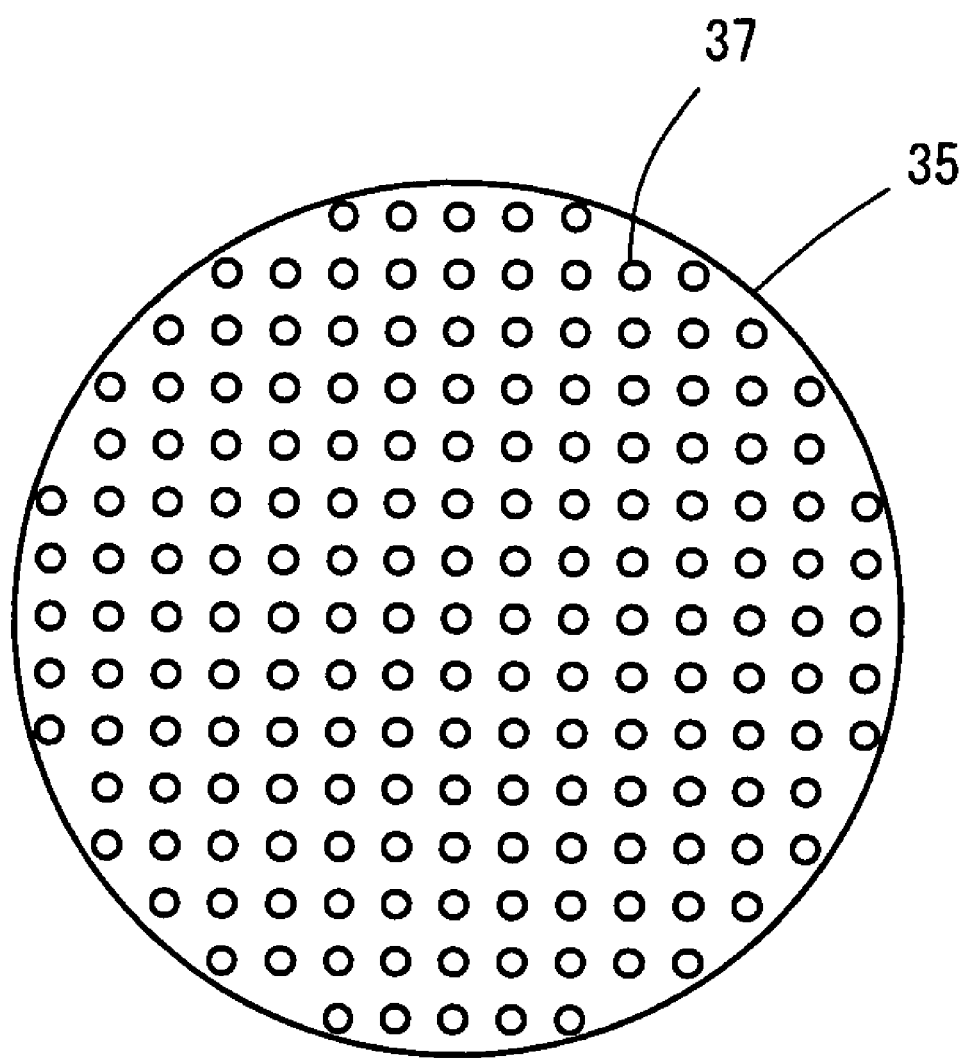

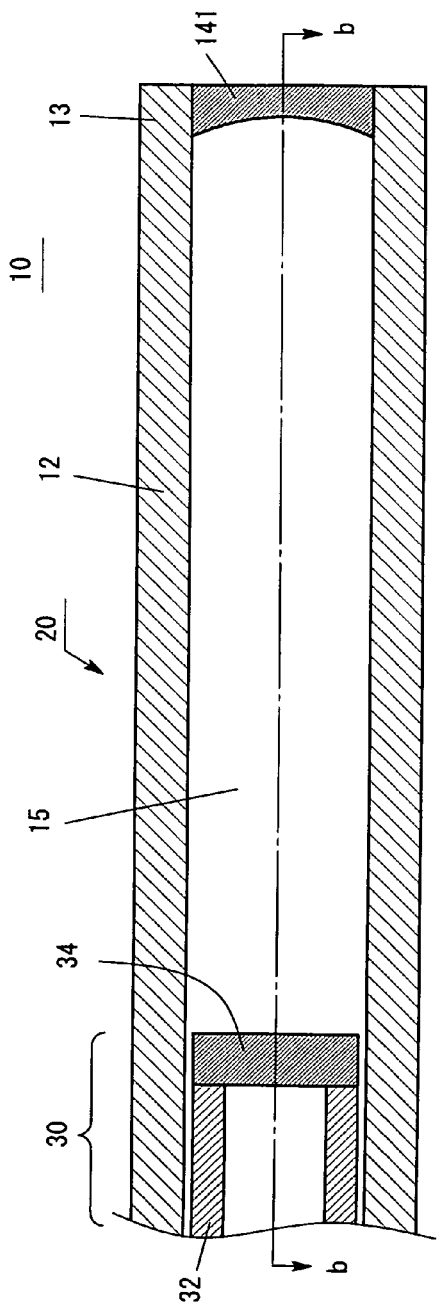

[Fig. 12]
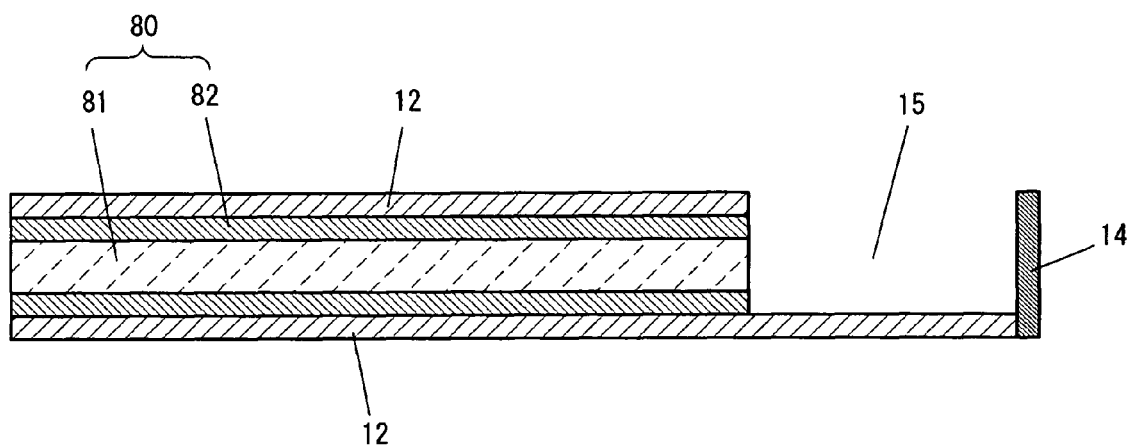

PARTICLE DENSITY MEASURING PROBE AND PARTICLE DENSITY MEASURING EQUIPMENT

BACKGROUND OF THE INVENTION

1. Field of the Invention

The present invention relates to a probe and a measuring device for measuring the density of particles such as atomics, molecules in a plasma atmosphere.

The present invention can be used for accurately measuring the particle density in the plasma atmosphere in order to accurately perform film deposition or etching using a plasma processing device or plasma.

2. Description of the Related Art

When a raw material gas is radicalized to deposit a thin film of a constituent of the gas on a processing target or to etch the processing target, in order to accurately control these processings, it is necessary to measure the density of atoms such as radicals in a plasma atmosphere to thereby control the generation of plasma. For this purpose, light is applied to a plasma atmosphere, and an atomic density is measured based on the absorption characteristic of this light.

As a device for measuring the atomic density, a device set forth in Japanese Unexamined Patent Application Publication No. 2004-354055 is known. According to this device, there are provided a hollow portion for introducing radicals formed at the front end of a tubular body, and a light source arranged in front of the hollow portion, and light is passed from the light source through the hollow portion and subjected to a spectroscopic analysis by a spectrometer provided at the base of the device. In this device, a lens is provided within the tubular body to make light linearly progress within the tubular body. Also, another device example is disclosed wherein at the base of a tubular body, a discharge light source is provided oppositely to a reflection plate arranged at the front end of the tubular body, and radicals are introduced into a hollow portion provided at the front end of the tubular body, wherein light is passed through the radicals and reflected by the reflection plate, and wherein the light is reflected in a 90 degree direction by a half mirror provided at the base of the tubular body, and a spectrometer is provided at a position forming an angle of 90 degrees relative to the light source. In this device also, a half-mirror is provided within the tubular body, and light is caused to linearly progress along an axis of the tubular body.

However, in each of the above-described devices, the tubular body does not guide light, but only performs a function as an enclosure that supports the discharge light source or the reflection plate provided at the front end of the tubular body and that protrudes the hollow portion introducing radicals from outside the reaction apparatus into a plasma atmosphere. Within the tubular body, a lens and the half mirror exist, which causes a problem that the diameter of the tubular body becomes large, as a matter of course. Consequently, the tubular body disturbs the state of plasma atmosphere, and has made it impossible to accurately measure a radical density in a true plasma atmosphere free of the tubular body. In addition, when measuring a radical density distribution within a plasma atmosphere while moving the tubular body, there has been a problem that an accurate radical density distribution cannot be measured since the large tubular body disturbs the state of plasma.

SUMMARY OF THE INVENTION

The present invention has been made to overcome the above-described conventional drawbacks, and the object of the present invention to realize a compact probe for measuring an atomic density without disturbing the state of plasma atmosphere, and also an atomic density measuring device using the above-described probe.

In a first aspect of the present invention, there is provided a particle density measuring probe for measuring the density of atoms or molecules in a plasma atmosphere by absorption spectroscopy, the particle density measuring probe comprising: a cylindrical light guiding member provided in a plasma atmosphere, the light guiding member including: a reflection plate for reflecting light that has propagated through the light guiding member, the reflection plate is provided at the front end of the light guiding member; and a plasma introducing portion in which, in a cross section perpendicular to the longitudinal direction of the light guiding member, a part devoid of a portion of wall surface is provided behind the reflection plate by a predetermined length in the longitudinal direction, and which allows the light passing through the part and atoms or molecules in the plasma atmosphere to make mutual contact; and a main body that guides light in an axial direction by total reflection by a side wall, the main body being located behind the plasma introducing portion.

Plasma is an aggregate of neutral particles such as electrons, atomic radicals, molecular radicals, atomic ions, molecular ions; or charged particles. The present invention is directed to a probe and a device for measuring the density in a plasma atmosphere, of particles having a predetermined absorption spectrum characteristic. Therefore, the measurement of densities of atomic radicals, molecular radicals, atomic ions, and molecular ions can be achieved. The present invention is characterized by providing the reflection plate at the front end and arranging the plasma introducing portion for inducting plasma behind the reflection plate, and by causing the main body to propagate light in the axial direction utilizing total reflection. As a result, the diameter of the probe can be reduced to a very small value, and with the probe inserted into the plasma atmosphere, a particle density distribution in the plasma atmosphere can be accurately measured without disturbing the state of plasma.

A second aspect of the present invention is characterized in that, in the first aspect, the main body of the light guiding member is constituted of a hollow tubular body having a reflection film formed on the inner surface thereof, and guides light in the axial direction using total reflection by the reflection film. In the present invention, the main body is constituted of a tubular body, and is configured to form the reflection film on its inner wall to thereby cause light progress along the axial direction using total reflection by the reflection film. This makes it possible to reduce the diameter of the main body to a small value, and to accurately measure a particle density distribution in a plasma atmosphere without disturbing the state of plasma. The inner diameter of the hollow tubular body is preferably 2 mm or less, and more preferably, 1 mm or less. Since the probe can be formed narrow like this, the particle density can be accurately measured without disturbing the state of plasma. The reflection film is formed by depositing a metal having a high reflectance, such as aluminum, gold, silver, or the like.

A third aspect of the present invention is characterized in that, in the first aspect, the main body of the light guiding member is an optical fiber comprising a core that guides light and a clad having a refraction index lower than that of the core, and guides light in the axial direction by generating total reflection on the interface between the core and the clad. That is, this aspect is characterized in that the main body is a fiber, and that total reflection is generated on the wall surface of the clad to thereby cause light to progress along the axial direction. This makes it possible to reduce the diameter of the main body to a small value, and to accurately measure a particle density distribution in a plasma atmosphere without disturbing the state of plasma. The diameter of the core of the fiber is preferably 2 mm or less, and more preferably, 1 mm or less. Since the probe can be formed narrow like this, the particle density can be accurately measured without disturbing the state of plasma.

A fourth aspect of the present invention is characterized in that, in any one of the first to third aspects, the light guiding member comprises a light propagating member for propagating light, and a cylindrical support member that supports the light guiding member at its outer peripheral side; and the plasma introducing portion is configured by forming a part that is devoid of a portion of wall surface is devoid in a cross section perpendicular to the longitudinal direction of the support member and that is free of the light guiding member, by a predetermined length in the longitudinal direction. That is, by providing the cylindrical support member that supports the light propagating member at its outer peripheral side, the plasma introducing portion capable of introducing plasma is provided to the front end portion of the support member, the plasma introducing portion being in a region devoid of a portion of wall surface and free of the light propagating member. By varying the length in the axial direction of the plasma introducing portion, the light absorption amount can be adjusted. That is, when a particle density is high, the length of the plasma introducing portion is reduced to thereby decrease the number of particles participant in light absorption, whereby the saturation of light absorption can be prevented. On the other hand, when a particle density is low, the length of the plasma introducing portion is increased to thereby increase the number of introduced particles, whereby the measurement sensitivity can be enhanced. In this construction, the outer diameter of the probe is the sum of an outer diameter of the light propagating member and wall-thicknesses of the support member. Letting an outer diameter of the light propagating member be 2.5 mm or less, and letting a wall-thickness of the support member be 1 mm, a probe outer diameter of 2.7 mm or less can be implemented. Also, letting an outer diameter of the light propagating member be 1.5 mm or less, the outer diameter of the probe becomes 1.7 mm or less, thus allowing an accurate measurement of particle density without disturbing the state of plasma atmosphere. In order to prevent disturbance of the state of plasma, it is desirable to use the probe with an outer diameter within a range of 1 to 2.5 mm. According to the present invention, this range can be realized.

In a fifth aspect of the present invention, there is provided a particle density measuring device comprising: the particle density measuring probe according to any one of the first to third aspects; and an optical system located on the side opposite to the installation side of the reflection plate in the main body, for making light incident on an input/output end face that allows light to enter it and that allows reflection light from the reflection plate to exit therefrom, the optical system including: a light source; a first lens for making light from the light source collimated light; a second lens for condensing light that has passed through the first lens on the input/output end face; and an angle-adjustable half mirror that causes light that has passed through the second lens to reflect on the input/output end face, and that causes light that has exited from the input/output end face to transmit toward a spectrometer; and a movement mechanism that changes the relative distance between the light source and the first lens.

In this device, a particle density can be measured only by inserting the cylindrical particle density measuring probe from outside the reaction apparatus for generating an atmosphere, into a plasma atmosphere. An optical system other than the particle density measuring probe is disposed outside the reaction apparatus. The use of the particle density measuring probe having a small diameter allows an accurate measurement of the spatial distribution of particle densities without disturbing the state of plasma.

Since the particle density measuring probe according to the present invention can have a diameter of 2.7 mm or less, and preferably 1.7 mm or less, it is possible to accurately measure a spatial distribution of particle densities without disturbing the state of plasma. In addition, by adjusting the length of the plasma introducing portion along the axial direction, the spatial distribution of particle densities can be measured at a maximum measurement sensitivity.

BRIEF DESCRIPTION OF THE DRAWINGS

FIG. 1 is a construction diagram showing a particle density measuring probe according to a specific embodiment of the present invention;

FIG. 2 is a sectional view of a support member of the particle density measuring probe;

FIG. 3 is a plan view showing the construction of a half mirror;

FIG. 4 is a construction diagram showing a particle density measuring device according to the present embodiment;

FIG. 5 is a construction diagram showing a reaction apparatus, the particle density measuring probe, and the particle density measuring device, each used for measurement of the atom radical density;

FIG. 6 is a characteristic diagram showing measured results of spatial distributions of atom radical densities within the reaction apparatus;

FIG. 7 is a characteristic diagram showing measured results of the relationship between the pressure of plasma atmosphere and the nitrogen radical density;

FIG. 8 is a characteristic diagram showing measured results of the relationship between the pressure of plasma atmosphere and the hydrogen radical density;

FIG. 9 is a characteristic diagram showing measured results of the relationship between the pressure of plasma atmosphere and the oxygen radical density;

FIG. 10 is a construction diagram of another example of window material at an end face of a light propagating member in the particle density measuring probe according to the present embodiment;

FIG. 11 is a construction diagram of another example of support member in the particle density measuring probe according to the present embodiment; and FIG. 12 is a construction diagram of a particle density measuring probe according to a second embodiment of the present invention.

DESCRIPTION OF THE PREFERRED EMBODIMENTS

Hereinafter, preferred embodiments of the present invention will be specifically described. In the present specification, the technical matter that is matter other than the contents specifically referred to in this specification and that is matter necessary for the practice of the present invention can be recognized as matter of workshop modification based on the conventional art for those skilled in the art. The present invention can be implemented based on the technical contents disclosed in the present specification and common general technical knowledge in the pertinent field.

Although the present invention is described hereinbelow based on the embodiments, the present invention is not limited to these embodiments. A technical idea grasped from the embodiments of the present invention is the scope of the present invention.

First Embodiment

FIG. 1 shows a particle density measuring probe 10 according to a first embodiment of the present invention. In FIG. 1, (a) is a top view, and (b) is a sectional view taken away along a line b-b in the above top view. A light guiding member 20 comprises: a cylindrical light propagating member 32; a cylindrical support member 12 that covers the outer periphery of the light propagating member 32; a reflection plate 14 provided at the front end of the support member; a plasma introducing portion 15 provided behind the reflection plate 14, for introducing plasma; and a main body 30 located on the light incident side further than the plasma introducing portion 15.

The cylindrical support member 12 is constituted of a ceramic in order to have a heat resisting property against a plasma atmosphere. Of course, the support member 12 may be constituted of stainless steel. The cylindrical support member 12 has an inner diameter of 1.7 mm, an outer diameter of 2.7 mm, a wall thickness of 0.5 mm, and a length of 300 mm. As shown in FIG. 2 (sectional view perpendicular to the axis), to the front end portion of the support member 12, there is provided the plasma introducing portion 15 that is devoid of a portion of wall surface and that can introduce plasma. An upper portion of the plasma introducing portion 15 is free of wall surface, and constitutes a window portion 16.

The reflection plate 14 that is contiguous to the plasma introducing portion 15, and that is provided at the front end of the support member 12, is formed by depositing Al and $MgF_2$ on a quartz disk with a diameter of 1.7 mm and a thickness of 0.5 mm. The main body 30 includes the support member 20 and the light propagating member 32 provided therein, and constitutes a hollow tubular body.

The light propagating member 32 is a hollow cylindrical body, and constituted of hollow glass. The light propagating member 32 has an inner diameter of 1 mm, an outer diameter of 1.6 mm, and a wall thickness of 0.3 mm. The light propagating member 32 can also be configured to have an outer diameter of 1 mm or less. The inner surface of the light propagating member 32 is covered with aluminum. To the front end of the light propagating member 32, a disk-shaped window material 34 constituted of $MgF_2$, having an outer diameter of 1.6 mm and a thickness of 1 mm is joined. As a result, the cylinder inner space of the light propagating member 32 is blocked from the outside.

Hereinbefore, the construction of the particle density measuring probe 10 has been described. Next, an optical system that makes light incident on an input/output end face 36 of the particle density measuring probe 10 will be explained. As shown in FIG. 4, this optical system is provided outside the reaction apparatus that generates plasma. Optical paths of the optical system are provided in an enclosure 66. The inside of the enclosure 66 has been evacuated to a vacuum. Hence, the hollow inside of the light propagating member 32 has also been evacuated to a vacuum, and this inside has a negative pressure relative to the plasma introducing portion 15. In this manner, by evacuating the optical paths to a vacuum, vacuum ultraviolet light is prevented from attenuation.

There is provided a movement mechanism 51 in which ball screws 52 provided in X, Y, and Z axis directions allow an installation base 53 to move along the X, Y, and Z axis directions. A light source 54 is mounted on the installation base 53 of the movement mechanism 51. Light emitted from the light source 54 is made incident on a first lens 55 and a subsequent second lens 56. The first lens 55, which has a focal length of 50 mm and a diameter of 20 mm, is a lens for collimating the light from the light source 54. The second lens 56, which has a focal length of 250 mm and a diameter of 20 mm, is a lens for making the collimated light that has passed through the first lens 55 incident on the input/output end face 36 of the light propagating member 36 by condensing light beams, with an incident angle relative to an optical axis being 1 degree or less.

A half mirror 60 is provided in the optical path from the second lens 56 up to the input/output end face 36. In order to make variable the position of the half mirror 60 in the optical paths, and reflection angle or transmission angle thereof, the half mirror 60 is configured so that its rotational angle and tilt angle are adjusted by a position/angle adjusting device 62 capable of adjusting the rotational angle, the tilt angle, and the spatial position of the half mirror 60. By adjusting the position, the rotational angle, and the tilt angle of the half mirror 60 by the angle adjusting device 62, the light from the light source 56 that has passed through the second lens 56 is reflected on the half mirror 60 in the 90 degree direction, whereby the incident position or the incident angle of the light propagating member 32 relative to the input/output end face 36 can be accurately adjusted. As shown in FIG. 3, the half mirror 60 is one formed by depositing Al on a disk made of $MgF_2$ in a dotted manner. As an alternative way, Al may be uniformly deposited on the disk, and minute holes free of Al may be formed by etching. By the above-described arrangement, the half mirror can be formed.

Light reflected by the reflection plate 14 transmits the half mirror 60, and is made incident on a third lens 57. The third lens 57 is configured so that the spatial position thereof is adjustable by a device 58 identical to the X, Y, and Z axis direction movement mechanism 51. The third lens 57 has a focal length of 56 mm, and a diameter of 15 mm. Light that has passed through the third lens 57 is made incident on a spectrometer 64. The third lens 57 is one for adjusting the incident position on a slit 65, of reflected light from the spectrometer 64, and the diameter of the light beam. This allows the wavelength dependence of the focal length due to differences among wavelengths of the light source 54 to be corrected.

By adjusting the X, Y, and Z axis direction movement mechanism 51 and the position/angle adjusting device 62 using such an optical system, it is possible to cause light from the light source 54 to enter from the input/output end face 36 of the light propagating member 32, along the optical axis of the light propagating member 32, with light beams condensed, and with an incident angle relative to the optical axis being 1 degree or less. As a consequence, the light propagates along the optical axis while making total reflection on the reflection film formed on the inner surface of the hollow tubular body of the light propagating member 32, and is emitted from the window material 34 to the plasma introducing portion 15. The light is absorbed by specified particles in this region, and reflected by the reflection plate 14, and after having been again absorbed by the specified particles, the light enters the light propagating member 32, from the window material 34. Then, by total reflection, the light propagates through the light propagating member 32 along the optical axis, and is emitted from the input/output end face 36 toward the half mirror 60. The light transmits through the half mirror 60 in the straight forward direction, and after having passed through the third lens 57, the light enters the spectrometer 64 via the slit 65. The light is subjected to a spectrum analysis by the spectrometer 64 to measure its absorbance.

The absorbance is obtained by a ratio with respect to the intensity when reflected light from the reflection plate 14 is spectroscoped by the spectrometer 64 using an optical system in which light from the light source 54 is adjusted to be identical, with the plasma introducing portion 15 being in a vacuum state. As the wavelength of light from the light source 54, a wavelength to be absorbed by particles to be measured is used. For example, when measuring a density of N radicals, light obtained by discharging nitrogen gas is used as the light source 54, and when measuring a density of H radicals, light obtained by discharging hydrogen gas is used as the light source 54. Thus, the absorbance can be measured by utilizing light absorption by the light-emission level of the identical atoms.

First, when measuring a density of H radicals, a self light-emission intensity of the H radicals is measured based on a spectrum of H radical light-emission as plasma emission. Then, light from the light source 54 is applied to the identical plasma, and based on the intensity of light that has passed through the plasma, a transmitted-light intensity is measured. By subtracting the self light-emission intensity from the transmitted-light intensity, a true transmitted-light intensity after having been absorbed by the H radicals can be obtained. Also, by subtracting the true transmitted-light intensity from the light source intensity of the light source 54, an absorption light intensity by the H radicals is obtained, and based on the ratio of this absorption light intensity by the H radicals with respect to the light source intensity, an absorption index by the H radicals can be measured. On the other hand, using light emission from N atoms having a spectrum close to that of H radicals, a background absorption index is obtained by the same method. Next, the absorption of light by plasma decreased as an exponential function of the product of a known optical path length L (absorption length) and the absorption index. Using this function, a background coefficient is obtained based on the background absorption index and the absorption length L. Here, the absorption length L is twice the length of the plasma introducing portion 15 along the axial direction. Next, light passing through the H radicals attenuates as an exponential function of the product between the sum of an absorption coefficient by the H radicals and a background absorption coefficient and the absorption length L. The value of this attenuation function provides an absorption index. As a result, using the measured absorption index and the above-described attenuation function, the absorption coefficient by the H radicals is obtained. Because this absorption coefficient and the density of H radicals are in a proportional relationship, the density of H radicals can be measured from the absorption coefficient. Since this method is known, and set forth in Japanese Unexamined Patent Application Publication No. 2004-354055, detailed description thereof is omitted.

Next, using the present particle density measuring device, particle densities were actually measured. The actual experimental device is shown in FIG. 5. In a radical generating chamber 71 connected to a reaction chamber 70, plasma is generated by a high frequency discharge of nitrogen gas, and N radicals was introduced into the reaction chamber 70. As is known in the art, ion species were removed by a mesh, and only the N radicals were introduced into the reaction chamber 70. While moving the spatial position of the particle density measuring probe 10 in the X, Y, and Z directions, densities of N radicals were measured. The particle density measuring probe 10 and its optical system are installed inside the enclosure, and the inside thereof has been evacuated to a vacuum. That is, the particle density measuring probe 10 and its optical system are configured to be able to propagate vacuum ultraviolet light without attenuation. Measurement results are shown in FIG. 6. Here, the horizontal axis denotes the distance from a radical source. Thus, density distributions of N radicals could be accurately measured without disturbing the state of plasma.

Furthermore, by changing the pressure within the reaction chamber, N radical densities were measured. Results are shown in FIG. 7. Likewise, out of plasma obtained by a discharge of hydrogen gas, only H radicals were introduced into the reaction chamber, and the pressure within the pressure chamber is changed to measure H radical densities. Results are illustrated in FIG. 8. Likewise, out of plasma obtained by a discharge of oxygen gas, only O radicals were introduced into the reaction chamber, and the pressure within the pressure chamber is changed to measure O radical densities. Results are illustrated in FIG. 9. In these measurements, as respective light sources, respective light beams obtained by discharging nitrogen gas, hydrogen gas, and oxygen gas, were used. In this manner, according to the particle density measuring probe and the particle density measuring device of the present invention, the spatial distribution of particle densities can be accurately measured without disturbing the state of plasma.

Modification

The window material 34 provided at the front end of the light propagating member 32 is formed as a disk made of $MgF_2$. In this case, plasma particles adhere onto the outer surface of the window material 34 and reduces the light-transmissive property with respect to detection light, so that there occurs a need for cleaning of the window material 34. With this being the case, as shown in FIG. 10, this window material 34 is configured as a capillary plate formed by making a large number of holes with a diameter of about 20 μm, in a glass plate 35 with a thickness of 1 mm and a diameter of 1.6 mm. For example, the ratio of the total area of the holes relative to the entire area of the glass plate, i.e., opening ratio is made about 50%. The inside of the enclosure 66 is evacuated to a vacuum, thereby evacuating the inner space of the light propagating member 32. Since light from the light source 54 is absorbed by the glass, it passes through only the holes 37 without passing through the glass plate portion free of holes 37. As a result, although plasma particles adhere onto the outer surface of the glass plate 35, they do not adhere to the holes 37. Therefore, there is no possibility that the transmissivity of light will attenuate with the course of measurements, which allows a high-accuracy measurement without the need to frequently perform cleaning. The hollow inside of the light propagating member 32 is in a vacuum state, and therefore, even if plasma particles pass through the holes 37, it is hard that they accumulate on the inner side surfaces of the holes 37. The measurement, therefore, can accurately be performed up to the extent that plasma particles adhere onto the inner side surfaces to thereby make smaller the diameters of the holes 37. In addition, radicals are distinguished by the holes 37, which allows the absorption length L of light to be accurately and constantly twice the distance between the glass plate 35 and the reflection plate 14, resulting in an improved measurement accuracy.

The front end of the light propagating member 32 may be opened without being provided with the window material 34 or the glass plate 35. In this case also, since the hollow inside of the light propagating member 32 has been evacuated to a vacuum, its conductance makes it difficult for plasma particles to enter the inside space. This allows the absorption length L to be constant as described above.

Furthermore, to the reflection plate 14, plasma particles adhere as well, and the reflectance of the reflection plate 14 decreases. With this being the situation, as in the case of the glass plate shown in FIG. 10, a plate having a large number of small holes with a similar diameter (about 20 μm) is installed in front of the reflection plate 14. In this case, the hole-length/diameter (aspect ratio) is made larger to thereby cause radicals to adhere onto the inner wall, whereby it is possible to prevent the radicals from reaching the surface of the reflection plate 14. As a result, since there is no possibility of reducing the reflectance of the reflection plate 14, the time period during which the reflection plate 14 can be used without the need for cleaning can be increased.

As shown in FIG. 11(b), in the support member 12, annular canopies 121 and 122 with a length of about 5 mm may be provided on both sides of the plasma introducing portion 15, that is, on the sides of the window material 34 and the reflection plate 14, respectively. These can also prevent the window material 34 and the reflection plate 14 from adhesion of plasma particles.

Also, as shown in FIG. 11(b), the reflection plate 14 may be formed as a concave mirror 141. As a consequence, light that after having been emitted from the end face (window material 34) of the light propagating member 32, has been diverged, is reflected by the concave mirror 141, and condensed on the end face (window material 34) of the light propagating member 32, whereby light can be made incident with a loss being small. This allows a high-accuracy measurement.

Second Embodiment

As shown in FIG. 12, the present embodiment constitutes the light propagating member not by a hollow tubular body, but by a glass fiber 80 composed of a core 81 and a clad 82 having a refraction index lower than that of the core 81. This glass fiber 80 is arranged within the support member 12 identical to that in the first embodiment. The constructions of the reflection plate 14 provided at the front end of the support member 12 and the plasma introducing portion 15 provided therebehind is the same as those in the first embodiment. The present glass fiber 80 can be constituted by hard glass in which the outer diameter of the core 81 is 0.7 mm, and that of the clad is 1.1 mm, the wall thickness of the support member 12 is 0.2 mm. Thus, the outer diameter can be made 1.5 mm. The use of this probe also allows the spatial distribution of particle densities to be accurately measured without disturbing the state of plasma.

What is claimed is:

1. A particle density measuring probe for measuring the density of atoms or molecules in a plasma atmosphere by absorption spectroscopy, the particle density measuring probe comprising:
a cylindrical light guiding member provided in the plasma atmosphere, the light guiding member including:
a reflection plate for reflecting light that has propagated through the light guiding member, the reflection plate is provided at the front end of the light guiding member; and
a plasma introducing portion in which, in a cross section perpendicular to the longitudinal direction of the light guiding member, a part devoid of a portion of wall surface is provided behind the reflection plate by a predetermined length in the longitudinal direction, and which allows mutual contact between the light passing through the part and atoms or molecules in the plasma atmosphere; and
a main body that guides light in an axial direction by total reflection by a side wall, the main body being located behind the plasma introducing portion.

2. The particle density measuring probe according to claim 1, wherein the main body of the light guiding member is constituted of a hollow tubular body having a reflection film formed on the inner surface thereof, and guides light in the axial direction using total reflection by the reflection film.

3. The particle density measuring probe according to claim 1, wherein the main body of the light guiding member is an optical fiber comprising a core that guides light and a clad having a refraction index lower than that of the core, and guides light in the axial direction by generating total reflection on the interface between the core and the clad.

4. The particle density measuring probe according to claim 1,
wherein the light guiding member comprises a light propagating member for propagating light, and a cylindrical support member that supports the light guiding member at its outer peripheral side; and
wherein the plasma introducing portion is configured by forming a part that is devoid of a portion of wall surface in a cross section perpendicular to the longitudinal direction of the support member and that is free of the light guiding member, by a predetermined length in the longitudinal direction.

5. The particle density measuring probe according to claim 2,
wherein the light guiding member comprises a light propagating member for propagating light, and a cylindrical support member that supports the light guiding member at its outer peripheral side; and
wherein the plasma introducing portion is configured by forming a part that is devoid of a portion of wall surface in a cross section perpendicular to the longitudinal direction of the support member and that is free of the light guiding member, by a predetermined length in the longitudinal direction.

6. The particle density measuring probe according to claim 3,
wherein the light guiding member comprises a light propagating member for propagating light, and a cylindrical support member that supports the light guiding member at its outer peripheral side; and
wherein the plasma introducing portion is configured by forming a part that is devoid of a portion of wall surface in a cross section perpendicular to the longitudinal direction of the support member and that is free of the light guiding member, by a predetermined length in the longitudinal direction.

7. A particle density measuring device, comprising:
a particle density measuring probe for measuring the density of atoms or molecules in a plasma atmosphere by absorption spectroscopy, the particle density measuring probe including:

a cylindrical light guiding member provided in the plasma atmosphere, the light guiding member including:

a reflection plate for reflecting light that has propagated through the light guiding member, the reflection plate is provided at the front end of the light guiding member; and a plasma introducing portion in which, in a cross section perpendicular to the longitudinal direction of the light guiding member, a part devoid of a portion of wall surface is provided behind the reflection plate by a predetermined length in the longitudinal direction, and which allows mutual contact between the light passing through the part and atoms or molecules in the plasma atmosphere; and a main body that guides light in an axial direction by total reflection by a side wall, the main body being located behind the plasma introducing portion; and an optical system located on the side opposite to the installation side of the reflection plate in the main body, for making light incident on an input/output end face that allows light to enter it and that allows reflection light from the reflection plate to exit therefrom, the optical system including:

a light source;

a first lens for making light from the light source collimated light;

a second lens for condensing light that has passed through the first lens on the input/output end face; and an angle-adjustable half mirror that causes light that has passed through the second lens to reflect on the input/output end face, and that causes light that has exited from the input/output end face to transmit toward a spectrometer; and a movement mechanism that changes the relative distance between the light source and the first lens.

8. The particle density measuring probe according to claim 7, wherein the main body of the light guiding member is constituted of a hollow tubular body having a reflection film formed on the inner surface thereof, and guides light in the axial direction using total reflection by the reflection film.

9. The particle density measuring probe according to claim 7, wherein the main body of the light guiding member is an optical fiber comprising a core that guides light and a clad having a refraction index lower than that of the core, and guides light in the axial direction by generating total reflection on the interface between the core and the clad.

* * * * *